United States Patent
Yerich et al.

(10) Patent No.: US 6,477,415 B1
(45) Date of Patent: Nov. 5, 2002

(54) AV SYNCHRONOUS CARDIAC PACING SYSTEM DELIVERING MULTI-SITE VENTRICULAR PACING TRIGGERED BY A VENTRICULAR SENSE EVENT DURING THE AV DELAY

(75) Inventors: Charles G. Yerich, Shoreview; Karen J. Kleckner, New Brighton; Carleen J. Juran, Shoreview, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/439,243

(22) Filed: Nov. 12, 1999

Related U.S. Application Data

(60) Provisional application No. 60/114,090, filed on Dec. 29, 1998, and provisional application No. 60/145,680, filed on Jul. 28, 1999.

(51) Int. Cl.[7] .............................................. A61N 1/362
(52) U.S. Cl. ........................................... 607/9; 607/25
(58) Field of Search ............................. 607/4, 9, 14, 25

(56) References Cited

U.S. PATENT DOCUMENTS

| | | | |
|---|---|---|---|
| 3,937,226 A | 2/1976 | Funke | 128/419 PG |
| 4,088,140 A | 5/1978 | Rockland et al. | 128/419 PG |
| 4,332,259 A | 6/1982 | McCorkle, Jr. | 128/786 |
| 4,354,497 A | 10/1982 | Kahn | 128/419 D |
| 4,458,677 A | 7/1984 | McCorkle, Jr. | 128/786 |
| 4,548,203 A | 10/1985 | Tacker, Jr. et al. | 128/419 D |

(List continued on next page.)

FOREIGN PATENT DOCUMENTS

| | | | |
|---|---|---|---|
| DE | 196 15 159 | 10/1997 | A61N/1/362 |
| WO | WO 99/29368 | 6/1999 | A61N/1/37 |
| WO | 9955415 | 11/1999 | |

OTHER PUBLICATIONS

Daubert et al., "Permanent Left Ventricular Pacing With Transvenous Leads Inserted Into The Coronary Veins", *Pace* (vol. 21, Part II, pp. 239–245, Jan. 1998).

(List continued on next page.)

*Primary Examiner*—Jeffrey R. Jastrzab
(74) *Attorney, Agent, or Firm*—Girma Wolde-Michael

(57) ABSTRACT

A pacing system for selectively sensing spontaneous ventricular cardiac depolarizations at first and second spaced apart ventricular sites during the time-out of an AV delay and delivering pace pulses to the spaced apart ventricular sites in a triggered pacing mode. The first and second ventricular sites are preferably right ventricular (RV) and left ventricular (LV) pace/sense electrode sites, and RV event and LV event signals are sensed at the RV and LV pace/sense electrodes. A V-A pacing escape interval and a ventricular refractory period, a trigger pace window, an upper rate interval and further post-event time periods are started upon a RV or LV sense event or a first ventricular pace pulse delivered upon time-out of the AV delay. A triggered ventricular pace pulse or pulses is delivered to one or both of the RV and LV pace/sense electrode sites upon detecting an RV sense event or LV sense event during the AV delay. In one triggered pacing mode, a RV or LV pace pulse is delivered upon a RV or LV sense event during the AV delay to one of the RV or LV pace/sense electrode sites. In another triggered pacing mode, a triggered pace pulse is delivered to the other one of the RV or LV pace/sense electrode sites after a triggered pacing delay timed from a non-refractory RV or LV sense event occurring during the AV delay. In still another triggered pacing mode, a first pace pulse is delivered upon a RV or LV sense event, the triggered pacing delay is timed out, and a second pace pulse is delivered to the other one of the RV or LV pace/sense electrode sites after time-out of the triggered pacing delay. Triggered ventricular pacing is disabled during the V-A escape interval. Such a system could be employed in pacemakers that are part of a cardio defibrillator system if desired.

10 Claims, 7 Drawing Sheets

U.S. PATENT DOCUMENTS

| | | | |
|---|---|---|---|
| 4,928,688 A | 5/1990 | Mower | 128/419 PG |
| 5,123,412 A | 6/1992 | Betzold | 607/17 |
| 5,174,289 A | 12/1992 | Cohen | 128/419 PG |
| 5,267,560 A | 12/1993 | Cohen | 607/25 |
| 5,387,228 A | 2/1995 | Shelton | 607/11 |
| 5,403,356 A | 4/1995 | Hill et al. | 607/14 |
| 5,514,161 A | 5/1996 | Limousin | 607/9 |
| 5,540,727 A | 7/1996 | Tockman et al. | 607/18 |
| 5,584,867 A | 12/1996 | Limousin et al. | 607/9 |
| 5,674,259 A | 10/1997 | Gray | 607/20 |
| 5,720,768 A | 2/1998 | Verbove-Nelissen | 607/9 |
| 5,728,140 A | 3/1998 | Salo et al. | 607/9 |
| 5,741,309 A | 4/1998 | Maares | 607/9 |
| 5,792,203 A | 8/1998 | Schroeppel | 607/30 |
| 5,797,970 A | 8/1998 | Pouvreau | 607/9 |
| 5,902,324 A | 5/1999 | Thompson et al. | 607/9 |
| 6,122,545 A * | 9/2000 | Struble et al. | 607/9 |

OTHER PUBLICATIONS

Cazeau et al., "Four Chamber Pacing in Dilated Cardiomyopathy", *Pace* (vol. 17, Part II, pp. 1974–1979, Nov. 1994).

Daubert et al., "Renewal of Permanent Left Atrial Pacing via the Coronary Sinus", *Pace* (vol. 15, Part II, NASPE Abstract 255, p. 572, Apr. 1992).

Daubert et al., "Permanent Dual Atrium Pacing in Major Intra–atrial Conduction Blocks: A Four Years Experience", *Pace* (vol. 16, Part II, NASPE Abstract 141, p. 885, Apr. 1993).

* cited by examiner

AV SYNCHRONOUS CARDIAC PACING SYSTEM DELIVERING MULTI-SITE VENTRICULAR PACING TRIGGERED BY A VENTRICULAR SENSE EVENT DURING THE AV DELAY

This patent application claims the benefit of U.S. Provisional Application Nos. 60/114090 filed Dec. 29, 1998 and 60/145860 filed Jul. 28, 1999.

CROSS-REFERENCE TO RELATED APPLICATIONS

Reference is hereby made to the following, commonly assigned, co-pending, U.S. Patent Applications which disclose common subject matter: Ser. No. 09/067,729 filed Apr. 28, 1998 for MULTIPLE CHANNEL, SEQUENTIAL, CARDIAC PACING SYSTEMS filed in the names of C. Struble et al.; Ser. No. (P-8398.00) filed on event date herewith for MULTI-SITE CARDIAC PACING SYSTEM HAVING CONDITIONAL REFRACTORY PERIOD filed in the names of K. Kleckner et al.; Ser. No. (P-8930.00) filed on even date herewith for BI-CHAMBER CARDIAC PACING SYSTEM EMPLOYING UNIPOLAR LEFT HEART CHAMBER LEAD IN COMBINATION WITH BIPOLAR RIGHT HEART CHAMBER LEAD in the names of B. Blow et al.; Ser. No. (P-8929.00) filed on even date herewith for CARDIAC PACING SYSTEM DELIVERING MULTI-SITE PACING IN A PREDETERMINED SEQUENCE TRIGGERED BY A SENSE EVENT in the names of C. Yerich et al.; Ser. No. (P-8928.00) filed on even date herewith for MULTI-SITE CARDIAC PACING SYSTEM HAVING TRIGGER PACE WINDOW in the names of C. Juran et al.; and Ser. No. (P-8401.00) filed on even date herewith for RECHARGE CIRCUITRY FOR MULTI-SITE STIMULATION OF BODY TISSUE filed in the names of B. Blow et al.

FIELD OF THE INVENTION

The present invention pertains to AV synchronous cardiac pacing systems, and particularly to delivering multi-site ventricular pacing triggered by a ventricular sense event detected at any ventricular site during the AV delay, particularly delivering pace pulses to the right and left ventricles triggered by a ventricular sense event in either the right or left ventricles during the AV delay only.

BACKGROUND OF THE INVENTION

In diseased hearts having conduction defects and in congestive heart failure (CHF), cardiac depolarizations that naturally occur in one upper or lower heart chamber are not conducted in a timely fashion either within the heart chamber or to the other upper or lower heart chamber. In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the right and left atria can result in left atrial flutter or fibrillation.

It has been proposed that various conduction disturbances involving both bradycardia and tachycardia of a heart chamber could benefit from pace pulses applied at multiple electrode sites positioned in or about a single heart chamber or in the right and left heart chambers in synchrony with a depolarization which has been sensed at least one of the electrode sites. It is believed that cardiac output can be significantly improved when left and right chamber synchrony is restored, particularly in patients suffering from dilated cardiomyopathy and CHF.

A number of proposals have been advanced for providing pacing therapies to alleviate these conditions and restore synchronous depolarization and contraction of a single heart chamber or right and left, upper and lower, heart chambers as described in detail in commonly assigned U.S. Pat. Nos. 5,403,356, 5,797,970 and 5,902,324 and in U.S. Pat. Nos. 5,720,768 and 5,792,203 all incorporated herein by reference. The proposals appearing in U.S. Pat. Nos. 3,937,226, 4,088,140, 4,548,203, 4,458,677, 4,332,259 are summarized in U.S. Pat. Nos. 4,928,688 and 5,674,259, all incorporated herein by reference. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514, 161, and 5,584,867, also all incorporated herein by reference.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", *PACE* (Vol. 16, Part II, NASPE Abstract 141, p. 885, April 1993); Daubert et al., "Permanent Left Ventricular Pacing With Transvenous Leads Inserted Into The Coronary Veins", *PACE* (Vol. 21, Part II, pp. 239–245, January 1998); Cazeau et al., "Four Chamber Pacing in Dilated Cardiomyopathy", *PACE* (Vol. 17, Part II, pp. 1974–1979, November 1994); and Daubert et al., "Renewal of Permanent Left Atrial Pacing via the Coronary Sinus", *PACE* (Vol. 15, Part II, NASPE Abstract 255, p. 572, April 1992), all incorporated herein by reference.

In the above-incorporated '324 patent, an AV synchronous pacing system is disclosed providing three or four heart chamber pacing through pace/sense electrodes located in or adjacent one or both of the right and left atrial heart chambers and in or adjacent to the right and left ventricular heart chambers. During an AV delay and during a V-A escape interval, a non-refractory ventricular sense event detected at either the right or left ventricular pace/sense electrodes starts a conduction delay window (CDW) timer. A ventricular pace pulse is delivered to the other of the left or right ventricular pace/sense electrodes at the time-out of the CDW if a ventricular sense event is not detected at that site while the CDW times out.

In certain patients, it is undesirable to deliver ventricular triggered pacing in response to a non-refractory ventricular sense event detected during the time-out of the V-A escape interval. Such ventricular sense events are detected from premature ventricular contractions (PVCs) that disrupt the normal synchronous contraction of the atria and ventricles. In some cases, the application of triggered ventricular pace pulses can be beneficial, but in other cases, the ventricular pace pulses may be pro-arrhythmic, that is, likely to trigger a tachyarrhythmia.

In certain dual chamber pacemakers, ventricular safety pacing (VSP) window of 110 msec (or a programmed PAV delay if less than 110 msec) is commenced with the PAV delay. A ventricular sense event occurring after time-out of the VSP window, but during the remaining period of the AV delay, simply terminates the AV delay and restarts the V-A escape interval. However, a ventricular sense event detected during the VSP window causes a ventricular pace pulse to be delivered to the single ventricular pacing site at the time-out of the 110 msec VSP window. At the same time, the AV delay is terminated and the V-A escape interval is restarted. The delivery of the ventricular sense event detected at the time-out of the 110 msec VSP window is intended to ensure that ventricular pacing is provided in cases where noise detected across the ventricular pace/sense electrodes due to the delivered atrial pace pulse would otherwise inhibit ventricular pacing. If the detected ventricular sense event is a true ventricular depolarization, the ventricular pace pulse is delivered harmlessly into the refractory period at that site in the ventricle rather than the following vulnerable period.

This delayed delivery of the ventricular pace pulse in the VSP triggered ventricular pacing mode is inappropriate under certain circumstances where patients would benefit from immediate triggered pacing during the AV delay.

Problems have been found with inappropriate location of sensing electrodes in patients with particularly long QRS waveforms. We believe that ventricular sensing may be enabled at only one particular chosen site or at a different site to avoid such problems. Particularly, both the mistaken double sensing of a single depolarization and polarization-induced sense amplifier blanking when inappropriate may be avoided by being able to determine where the device will sense the depolarization wavefront to the extent possible with the several electrodes available in multi-site systems. For example, if a depolarization has started well before it is sensed and has traversed one of the pacing electrodes several milliseconds (ms) earlier, pacing as soon as possible is preferred over waiting the 110 ms after sensing at the chosen but second to sense electrode. In thinking about how to appropriately enable particular sense electrodes, we have also found that the use of trigger pacing during the AV delay may be preferred over standard ventricular safety pacing for systems that employ more than one pace/sense electrode in the ventricle. In preferred embodiments this triggering would occur only after an atrial pace (not an atrial sense) to make it more specifically a safety feature.

As we have begun to describe it, there is a need for an optimized AV sequential, multi-site ventricular pacing system that provides ventricular triggered pacing throughout the AV delay and avoids precipitating arrhythmias at other times.

SUMMARY OF THE INVENTION

The present invention provides a pacing system for selectively sensing spontaneous ventricular cardiac depolarizations at first and second spaced apart ventricular sites during the time-out of an AV delay and delivering ventricular pace pulses to one or both of the spaced apart ventricular sites in a triggered pacing mode. The first and second ventricular sites are preferably right ventricular (RV) and left ventricular (LV) pace/sense electrode sites, and RV event and LV event signals are sensed at the RV and LV pace/sense electrodes. A V-A pacing escape interval is started upon a RV or LV sense event or a first ventricular pace pulse delivered upon time-out of the AV delay. A triggered ventricular pace pulse or pulses is delivered to one or both of the RV and LV pace/sense electrode sites upon detecting an RV sense event or LV sense event at any time during the AV delay. Triggered ventricular pacing is disabled during the V-A escape interval.

In a preferred triggered pacing mode, a first pace pulse is delivered without delay upon a RV or LV sense event, the triggered pacing delay is timed out, and a second pace pulse is delivered to the other one of the RV or LV pace/sense electrode sites after time-out of the triggered pacing delay. In another triggered pacing mode, a RV or LV pace pulse is delivered without delay upon a RV or LV sense event during the AV delay to one of the RV or LV pace/sense electrode sites.

The present invention provides optimized AV sequential, multi-site ventricular pacing system that delivers triggered ventricular pacing to one or more ventricular pacing sites at any time throughout the AV delay and avoids precipitating arrhythmias at other times.

The present invention is preferably implemented in AV synchronous pacing systems for providing atrial and ventricular bi-chamber pacing of at least one of the right and left atria and both the right and left ventricles. The present invention is preferably implemented into an external or implantable pulse generator and lead system selectively employing right and left heart, atrial and ventricular leads. The AV synchronous embodiments may be implemented into an IPG or external pulse generator and lead system providing right and left ventricular pacing and sensing and either both right and left atrial pacing or just right or left atrial pacing and sensing. Alternatively, the invention can be implemented in IPGs or external pulse generators and lead systems having hard wired connections and operating modes that are not as programmable.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail in FIGS. 2 and 3 in the context of an AV sequential, bi-ventricular, pacing system operating in demand, atrial tracking, and triggered pacing modes in accordance with FIGS. 4 through 6A–6B for restoring synchrony in depolarizations and contraction of left and right ventricles in synchronization with atrial sensed and paced events for treating bradycardia in those chambers. This embodiment of the invention is programmable to operate as a three or four channel pacing system having an AV synchronous operating mode for restoring upper and lower heart chamber synchronization and right and left atrial and/or ventricular chamber depolarization synchrony.

It should be appreciated that the present invention may be utilized particularly to treat patients suffering from CHF with or without bradycardia. The pacing system of the present invention may also may be incorporated into an anti-tachyarrhythmia system including specific high rate pacing and cardioversion shock therapies for providing staged therapies to treat a diagnosed arrhythmia.

Figure 1:
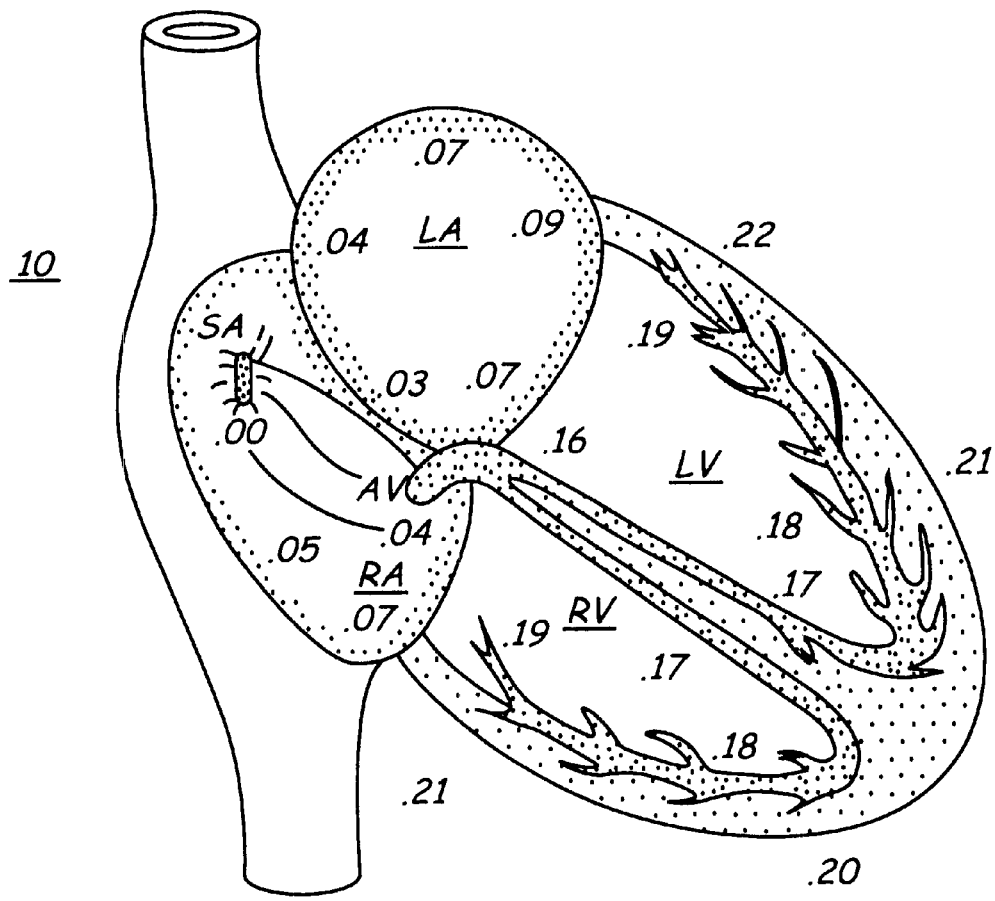
FIG. 1 is an illustration of transmission of the cardiac depolarization waves through the heart in a normal electrical activation sequence.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the cardiac veins. FIG. 1 is an illustration of transmission of the cardiac depolarization waves through the RA, LA, RV and LV in a normal electrical activation sequence at a normal heart rate with the conduction times exhibited thereon in seconds. The cardiac cycle commences normally with the generation of the depolarization impulse at the SA Node in the right atrial wall and its transmission through the atrial conduction pathways of Bachmann's Bundle and the Internodal Tracts at the atrial level into the left atrial septum. The RA depolarization wave reaches the Atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent the RV or LV exceeds a threshold amplitude, it is detected as a sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced CHF and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak—peak asynchrony can range from 80 to 200 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions.

In accordance with a first embodiment of the present invention, a method and apparatus is provided to restore the depolarization sequence of FIG. 1 and the synchrony between the right and left ventricular heart chambers that contributes to adequate cardiac output. This restoration is effected through providing optimally timed cardiac pace pulses to the right and left ventricles as necessary and to account for the particular implantation sites of the pace/sense electrodes in relation to each heart chamber while maintaining AV synchrony. The present invention efficiently provides pacing of at multiple ventricular pacing sites in a triggered pacing mode in response to a ventricular sense event detected at either ventricular pace/sense electrode site during the AV delay only.

Figure 2:
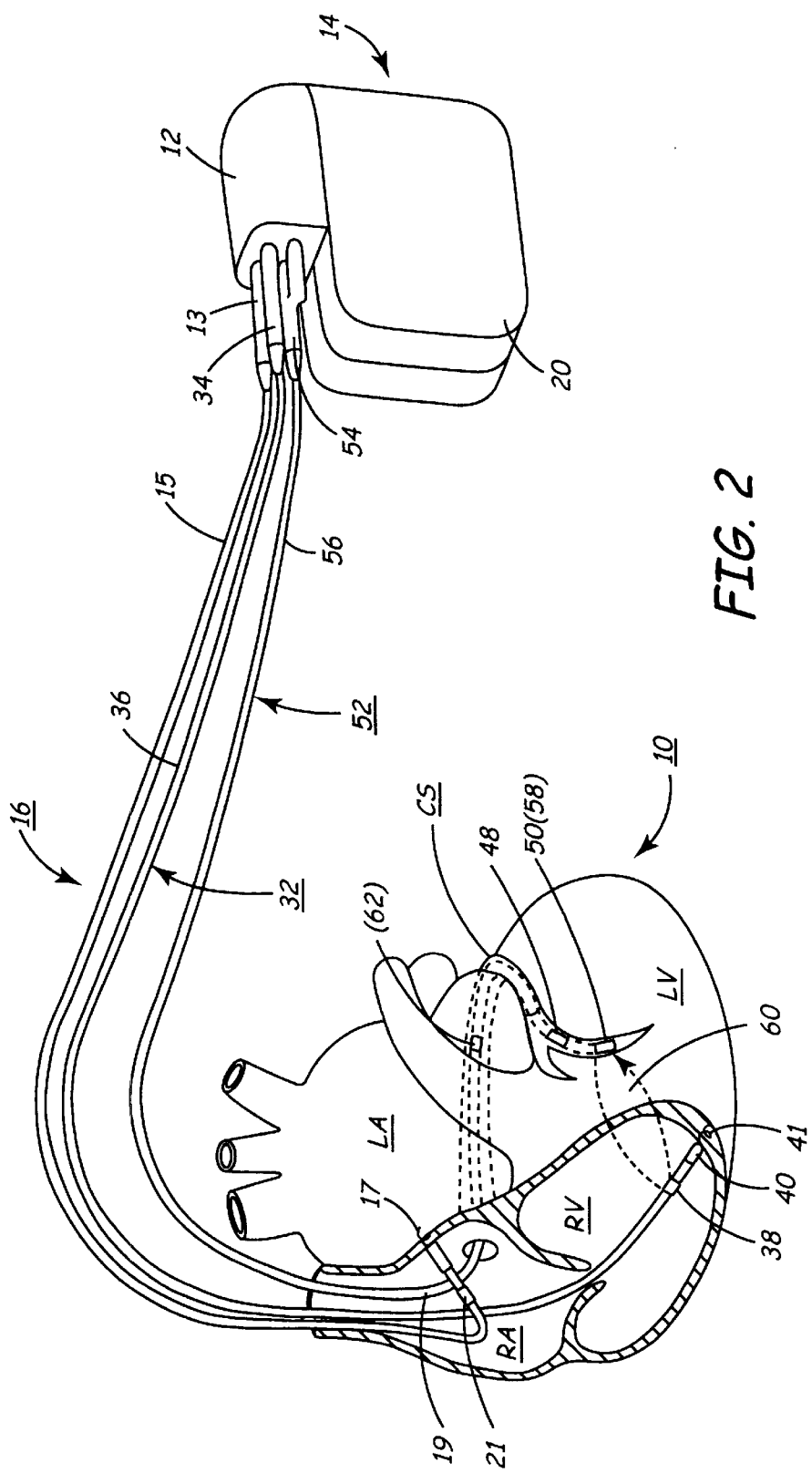
FIG. 2 is a schematic diagram depicting a three channel, atrial and bi-ventricular, pacing system in which the present invention is preferably implemented.

FIG. 2 is a schematic representation of an implanted, three channel cardiac pacemaker of the above noted types for restoring AV synchronous contractions of the atrial and ventricular chambers and simultaneous or sequential pacing of the right and left ventricles. The Implantable Pulse Generator IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiorly in a branching vessel of the great vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to place the distal LV CS pace/sense electrode 50 in a vein branching inferiorly from the coronary sinus 48.

Preferably, the distal, LV CS active pace/sense electrode 50 is paired with the proximal ring RV indifferent pace/sense electrode 38 for delivering LV pace pulses across the bulk of the left ventricle and the intraventricular septum. The distal LV CS active pace/sense electrode 50 is also preferably paired with the distal tip RV active pace/sense electrode 40 for sensing across the RV and LV as described further below.

Moreover, in a four chamber embodiment, LV CS lead 52 could bear a proximal LA CS pace/sense electrode positioned along the lead body to lie in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

Figure 3:
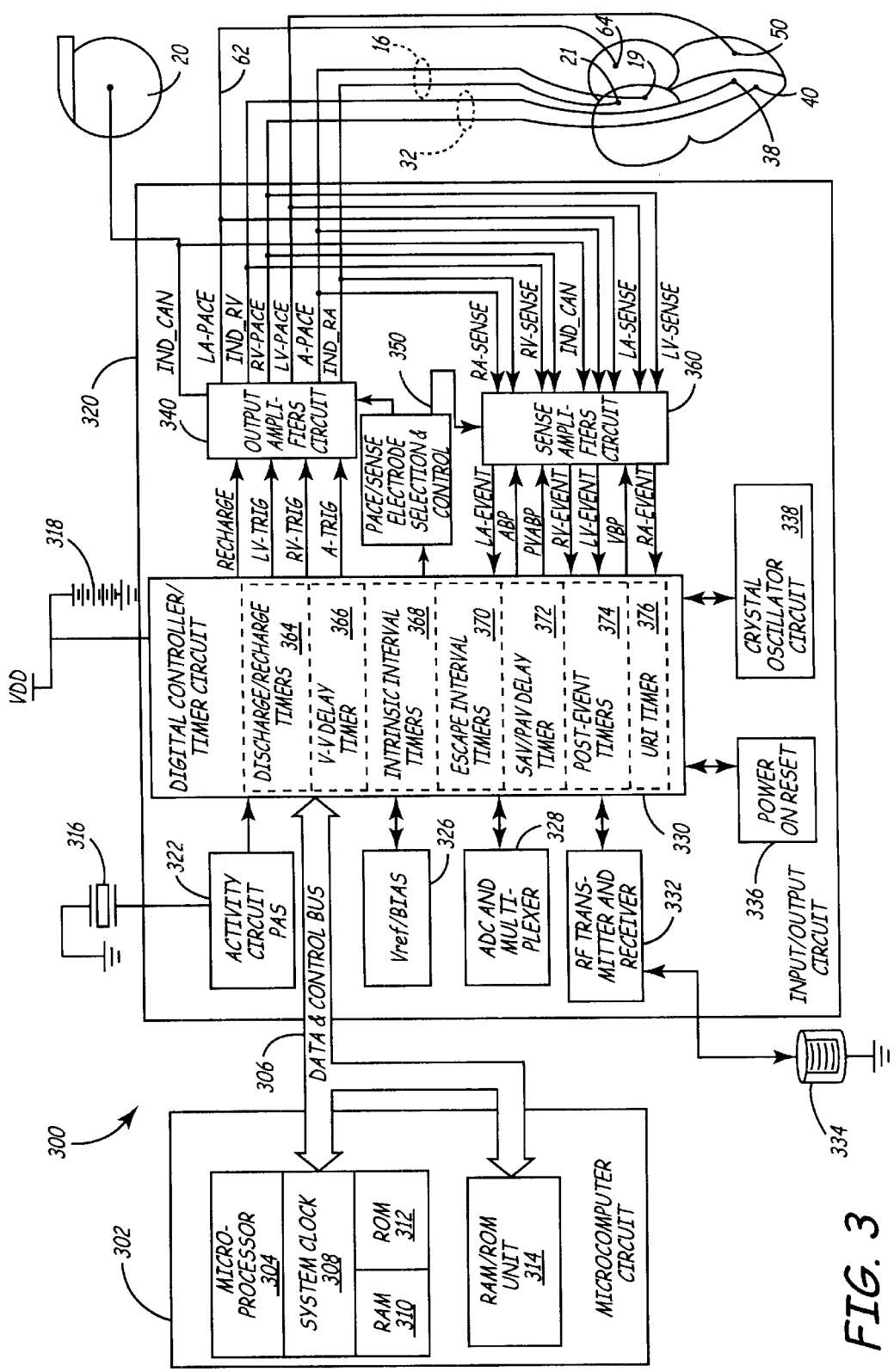
FIG. 3 is a simplified block diagrams of one embodiment of IPG circuitry and associated leads employed in the system of FIG. 2 for providing four pacing channels that are selectively programmed in bi-atrial and/or bi-ventricular pacing modes.

Typically, in pacing systems of the type illustrated in FIGS. 2 and 3, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors. Separate or shared indifferent pace and sense electrodes can also be designated in pacing and sensing functions. For convenience, the following description separately designates pace and sense electrode pairs where a distinction is appropriate.

FIG. 3 depicts bipolar RA lead 16, optional unipolar LA lead 62, bipolar RV lead 32, and unipolar LV CS lead 52 coupled with an IPG circuit 300 having programmable modes and parameters and a telemetry transceiver of a DDDR type known in the pacing art. A unipolar LA pace/sense electrode 64 is provided at the distal end of the LA CS lead 62. The unipolar LA lead 62 may also be a CS lead and may be formed as part of the LV CS lead 52 as described above. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, and the sense amplifiers circuit 360, as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the implantable pulse generator housing 18 and may take the form of a piezoelectric crystal transducer as is well known in the art and its output signal is processed and used as the RCP. A timed interrupt, e.g., every two seconds, may be provided in order to allow the microprocessor 304 to analyze the output of the activity circuit PAS 322 and update the basic V-A (or A-A or V-V) escape interval employed in the pacing cycle.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-PACE, RV-PACE, LV-PACE signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include discharge/recharge timers 364, V-V delay timer 366, an intrinsic interval timer 368 for timing elapsed V-EVENT to V-EVENT intervals or V-EVENT to A-EVENT intervals, escape interval timers 370 for timing A-A, V-A, and/or V-V pacing escape intervals, an AV delay interval timer 372 for timing an AV delays from a preceding A-EVENT (SAV) or A-PACE (PAV), a post-ventricular timer 374 for timing post-ventricular time periods, and an upper rate interval (URI) timer 376. RHC pace trigger and sense events are typically used for starting and resetting these intervals and periods. However, it would be possible to allow the physician to select and program trans-chamber or LHC pace trigger and sense events for these timing purposes.

Microcomputer 302 controls the operational functions of digital controller/timer circuit 330, specifying which timing intervals are employed, and setting at least the programmed-in base timing intervals, via data and control bus 306. Digital controller/timer circuit 330 starts and times out these intervals and delays for controlling operation of the atrial and ventricular sense amplifiers in sense amplifiers circuit 360 and the atrial and ventricular pace pulse generators in output amplifiers circuit 340.

The post-event timers 374 time out the post-ventricular time periods following an RV-EVENT or LV-EVENT or a RV-PACE or LV-PACE and post-atrial time periods following an A-EVENT or A-PACE. The durations of the post-event time periods may also be selected as programmable parameters stored in the microcomputer 302. The post-ventricular time periods include the PVARP, a post-atrial ventricular blanking period (PAVBP), a ventricular blanking period (VBP), a ventricular refractory period (VRP), and a conditional ventricular refractory period (CVRP). The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV or PAV delay started by an A-EVENT or an A-PACE.

It should be noted that the starting of the post-atrial time periods and the AV delays can be commenced substantially simultaneously with the start or end of the A-EVENT or A-PACE. Similarly, the starting of the post-ventricular time periods and the V-A escape interval can be commenced substantially simultaneously with the start or end of the V-EVENT or V-PACE.

The microprocessor 304 also optionally calculates AV delays, post-ventricular time periods, and post-atrial time periods which vary with the sensor based escape interval established in response to the RCP(s) and/or with the intrinsic atrial rate. The variable AV delays are usually derived as a fraction of a maximum AV delay set for the pacing lower rate (i.e., the longest escape interval).

The output amplifiers circuit 340 contains a RA pace pulse generator, a LA pace pulse generator, a RV pace pulse generator and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates a RV-TRIG or LV-TRIG signal at the end of an AV delay provided by AV delay interval timer 372. Similarly, in order to trigger a right or left atrial pacing or RA-PACE pulse or LA-PACE pulse, digital controller/timer circuit 330 generates an RA-TRIG or LA-TRIG signal at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator, LA pace pulse generator, RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing as described below.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pace pulse to any of the pace electrodes of the pacing system to avoid saturation of the sense amplifiers.

The sense amplifiers circuit 360 includes blanking circuits for uncoupling the selected pairs of the lead conductors and the IND_CAN electrode 20 from the inputs of the RA sense amplifier, LA sense amplifier, RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier, LA sense amplifier, RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

To simplify the description of FIGS. 4 through 6A–6B, it will be assumed that the following references to an "A-EVENT" and "A-PACE" will be the RA-EVENT and RA-PACE, respectively, if there is no LA pacing or sensing provided or programmed on, or will be a programmed one of the RA-EVENT or LA-EVENT and RA-PACE or LA-PACE, respectively. The A-EVENT could also be the output sense event signal of a single atrial sense amplifier coupled to active pace/sense electrodes 19 and 64.

The possible operating modes of IPG circuit 300 are depicted in the flow chart of FIG. 4 and described as follows. The particular operating mode of the present invention is a programmed or hard wired sub-set of the possible operating modes Is also described below. The AV delay is started in step S100 when a P-wave outside of refractory is sensed across the selected atrial sense electrode pair during the V-A escape interval (an A-EVENT) as determined in step S134 or an A-PACE pulse is delivered to the selected atrial pace electrode pair in step S118. The AV delay can be a PAV or SAV delay, depending upon whether it is started on an A-PACE or an A-EVENT, respectively, and is timed out by the SAV/PAV delay timer 372. The SAV or PAV delay is terminated upon a non-refractory RV-EVENT or LV-EVENT output by a ventricular sense amplifier prior to its time-out.

The post-event timers 374 are started to time out the post-ventricular time periods and the TRIG_PACE window, and the V-A escape interval timer 370 is started to time out the V-A escape interval in step S104 if the SAV or PAV delay times out in step S102 without the detection of a non-refractory RV-EVENT or LV-EVENT. The TRIG_PACE window inhibits triggered pacing modes in response to a sense event occurring too early in the escape interval and is described in greater detail in the above-referenced '(P-8928) application.

Either a programmed one or both of the RV-PACE and LV-PACE pulses are delivered in step S106 (as shown in the flow chart of FIG. 5) to selected RV and LV pace electrode pairs, and the V-A escape interval timer is timed out in step S116. When both of the RV-PACE and LV-PACE pulses are delivered, the first is referred to as V-PACE1, the second is referred to as V-PACE2, and they are separated by a VP-VP delay. As described in greater detail below in reference to FIGS. 6A–6B, if a bi-ventricular pacing mode is programmed in step S106, it can be selectively programmed in a left-to-right or right-to-left ventricle pacing sequence wherein the first and second delivered ventricular pace pulses are separated by separately programmed VP-VP delays. The VP-VP delays are preferably programmable between about 0 msec and about 80 msec.

Figure 6A:
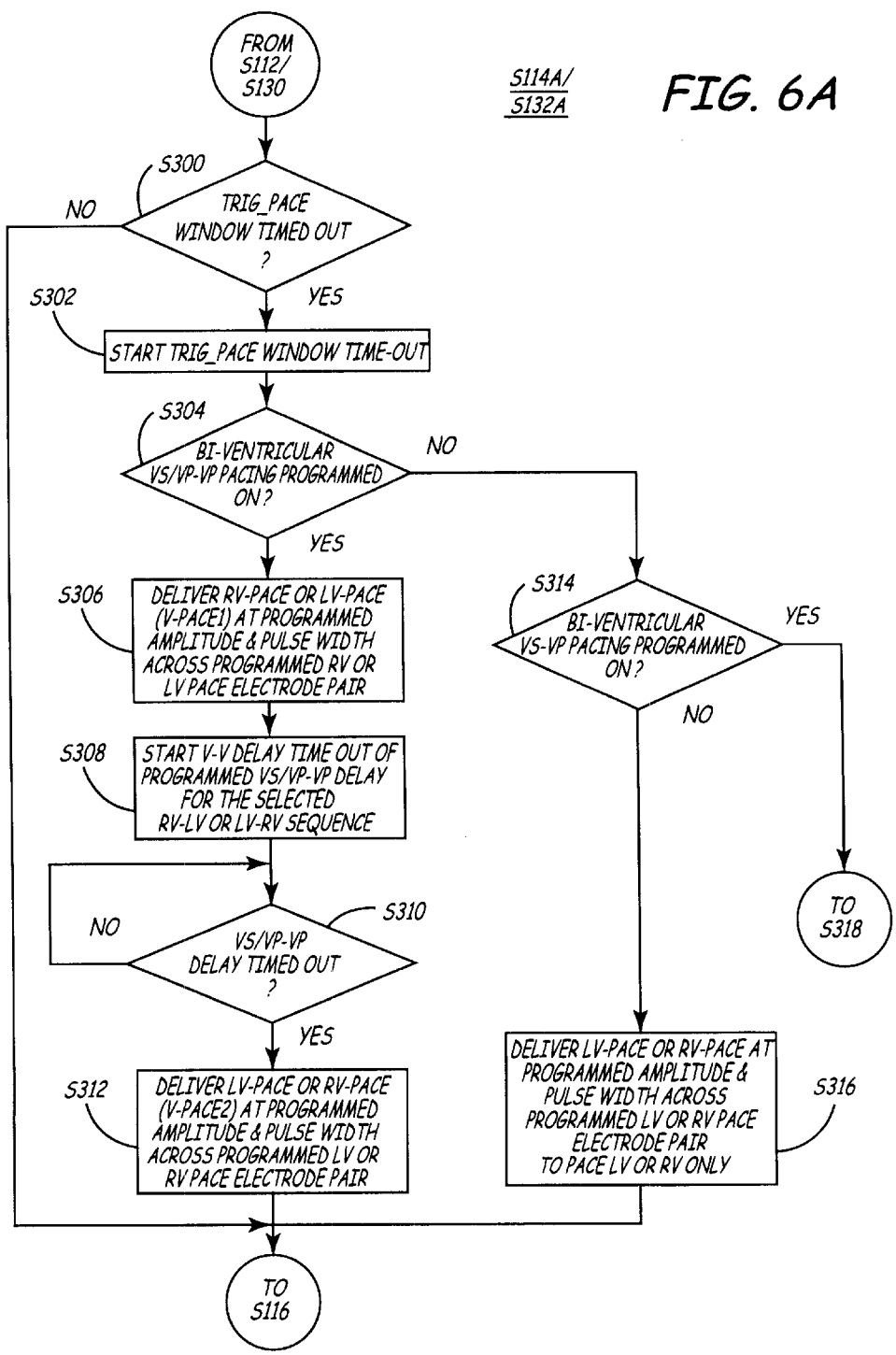
FIG. 6A–6B is a flow chart illustrating the steps of delivering ventricular pace pulses following a ventricular sense event during the time-out of an AV delay or the V-A escape interval in FIG. 4.
Figure 6B:
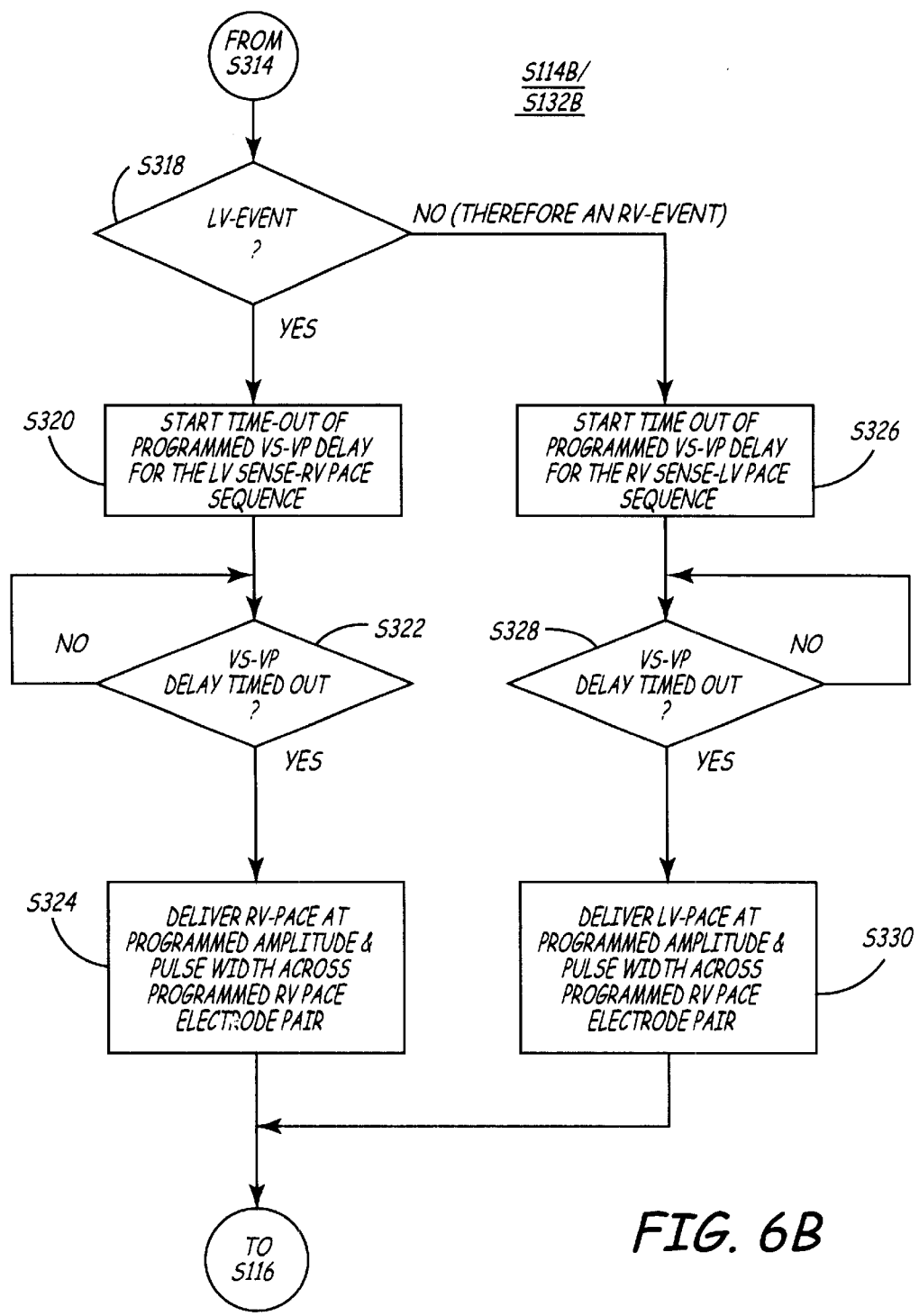

Returning to step S102, the AV delay is terminated if an RV-EVENT or LV-EVENT (collectively, a V-EVENT) is generated by the RV sense amplifier or the LV sense amplifier in step S108. The time-out of the V-A escape interval and the post-ventricular time periods are started in step S110 in response to the V-EVENT. In step S112, it is determined whether a ventricular triggered pacing mode is programmed to be operative during the AV delay. In accordance with the present invention, a ventricular triggered pacing mode is programmed on, and it is undertaken and completed in step S114 (FIGS. 6A–6B). Any VSP mode that may otherwise be available is programmed off. The time-out of the TRIG_PACE window is commenced in step S113 simultaneously with the time-out of the V-A escape interval and post-event time periods in step S110.

If the V-A atrial escape interval is timed out by timer 370 in step S116 without a non-refractory A-EVENT being sensed across the selected pair of atrial sense electrodes, then the A-PACE pulse is delivered across the selected RA pace electrode pair in step S118, the AV delay is set to PAV in step S120, and the AV delay is commenced by AV delay timer 372. If a non-refractory A-EVENT is generated as determined in steps S122 and S134, then the V-A escape interval is terminated. The ABP and ARP are commenced by post-event timers 374 in step S136, the AV delay is set to the SAV in step S138, and the SAV delay is started in step S100 and timed out by SAV/PAV delay timer 372.

Assuming that the normal activation sequence is sought to be restored, a programmed SAV and PAV delay corresponding to a normal AV conduction time from the AV node to the bundle of His are used or a calculated SAV and PAV delay is calculated in relation to the prevailing sensor rate or sensed intrinsic heart rate and are used by SAV/PAV delay timer 372.

If an RV-EVENT or LV-EVENT or a collective V-EVENT sensed across the RV tip sense electrode and the LV sense electrode (for simplicity, all referred to as a V-EVENT) is detected in step S123 during the time-out of the V-A escape interval, then, it is determined if it is a non-refractory V-EVENT or a refractory V-EVENT in step S124. If the V-EVENT is determined to be a refractory V-EVENT in step S124, then it is employed in the CVRP processing step S126 which is described in detail in the above-referenced (P-8398.00) application. If the V-EVENT is determined to be a non-refractory V-EVENT in step S124, then the TRIG_PACE window is started or restarted, the V-A escape interval is restarted, and the post-ventricular time periods are restarted in step S128.

In step S130, it is determined whether a ventricular triggered pacing mode is programmed to be operative during the V-A escape interval. In accordance with the present invention, ventricular triggered pacing during the V-A escape interval is not programmed on or not provided in the pacing system when triggered ventricular pacing is inappropriate for the patient. Steps S130 and S132 are merely included herein to complete the disclosure of one form of an AV synchronous pacing system in which the present invention may be incorporated. It will be understood that the present invention can be incorporated into an AV synchronous pacing system that does not include steps S130 and S132.

If a ventricular triggered pacing during the V-A escape interval is in the pacing system and is programmed on, then it is undertaken and completed in step S132 (FIGS. 6A–6B). If triggered pacing is not programmed on as determined in step S130, then no ventricular pacing is triggered by the sensed non-refractory V-EVENT during the V-A escape interval. The time-out of the TRIG_PACE window is commenced in step S131 simultaneously with the time-out of the V-A escape interval and post-event time periods in step S128.

Figure 5:
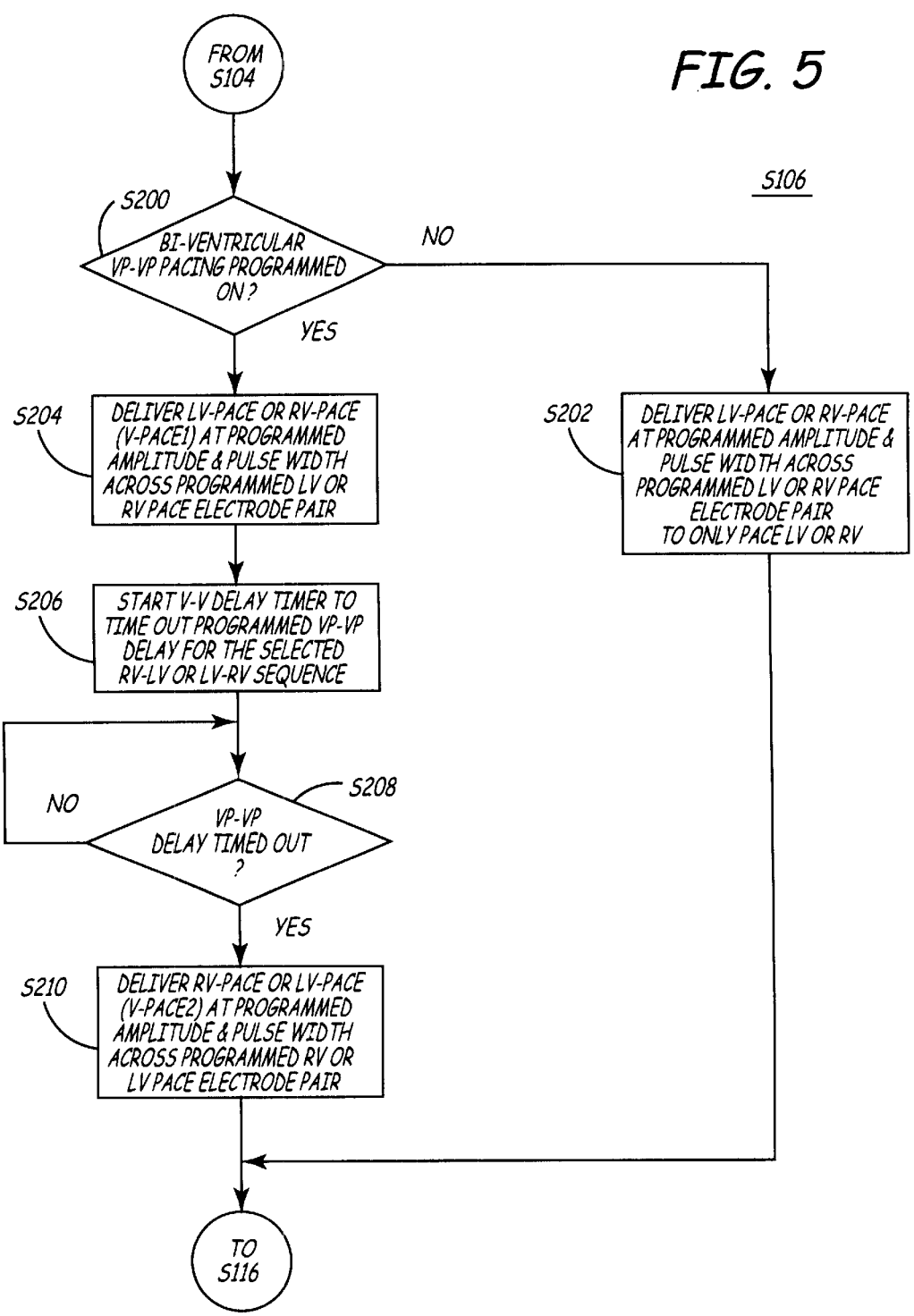
FIG. 5 is a flow chart illustrating the steps of delivering ventricular pace pulses following time-out of an AV delay in FIG. 4.

FIG. 5 depicts the step S106 in greater detail, and FIGS. 6A–6B depict the steps S114 and S132 in greater detail. If a VP-VP pacing mode is programmed on in step S106, it can be selectively programmed in a left-to-right or right-to-left ventricle sequence, wherein the first and second delivered ventricular pace pulses (V-PACE1 and V-PACE2) are separated by separately programmed VP-VP delays. If a bi-ventricular triggered pacing mode is programmed on in either or both of steps S114 and S132, it can be selectively programmed to immediately pace the ventricle from which the V-EVENT is sensed or a fixed or programmed ventricle regardless of where the V-EVENT is sensed with a V-PACE1. Then, the V-PACE2 is generated to synchronously pace the other ventricle after a programmed VS/VP-VP delay. Or, the triggered pacing mode can be selectively programmed in either or both of steps S114 and 132 to only synchronously pace the other ventricle than the ventricle from which the V-EVENT is sensed with V-PACE2 after separately programmable VS-VP delays, depending on the right-to-left or left-to-right sequence. All of these VP-VP, VS/VP-VP, and VS-VP delays are preferably programmable between nearly 0 msec and about 80 msec. As a practical matter, the minimum VS/VP-VP, and VP-VP delays may be set to one half the system clock cycle in order to avoid simultaneous delivery of RV-PACE and LV-PACE pulses. The pace pulse width is typically programmable between about 0.5 msec and 2.0 msec, and the pace pulse amplitude is typically programmable between 0.5 and 7.5 volts. The system clock provides a full clock cycle of about 8.0 msec. Therefore, the minimum VP-VP delay is set at a half clock cycle or about 4.0 msec.

As shown in FIG. 5, the IPG circuit 300 of FIG. 3 can be programmed to either only deliver a single RV-PACE or LV-PACE (V-PACE1) or the pair of RV-PACE and LV-PACE pulses (V-PACE1 and V-PACE2) separated by the VP-VP delay timed out by V-V delay timer 366. If delivery of only a single RV-PACE or LV-PACE is programmed as determined in step S200, then it is delivered in step S202.

If VP-VP pacing is programmed on in step S200, then V-PACE1 is delivered in step S204 in the programmed RV-LV or LV-RV sequence. Again, the RV-PACE pulse is typically delivered across the active RV tip electrode 40 and one of the available indifferent electrodes that is programmed and selected through the pace/sense electrode selection and control 350 depending upon which are present in the pacing system and the RV pacing vector that is desired as set forth above. And, the LV-PACE pulse is delivered across the active LV pace electrode 50 and the IND_RV pace electrode 38 in the trans-ventricular pacing path 60. The V-PACE1 pace pulse is delivered at a programmed pulse energy dictated by the programmed voltage and pulse width.

The V-V delay timer 366 is loaded with the programmed VP-VP delay and starts to time out in step S206. If the RV-PACE pulse is V-PACE1, then a programmed VP-VP delay is timed in V-V delay timer 366. The LV-PACE pulse is delivered as V-PACE2 in the LV pacing path 60 between the active LV pace electrode 50 and IND_RV pace electrode 38 in step S210 after time-out of the programmed VP-VP delay in step S208. Conversely, if the LV-PACE pulse is the first to be delivered (V-PACE1) in the pacing path 60, then a programmed VP-VP delay is timed in V-V delay timer 366. The RV-PACE pulse is then delivered as V-PACE2 typically across the active RV pace electrode 40 and the programmed indifferent electrode in step S210 after time-out of the programmed VP-VP delay in step S208.

Figure 4:
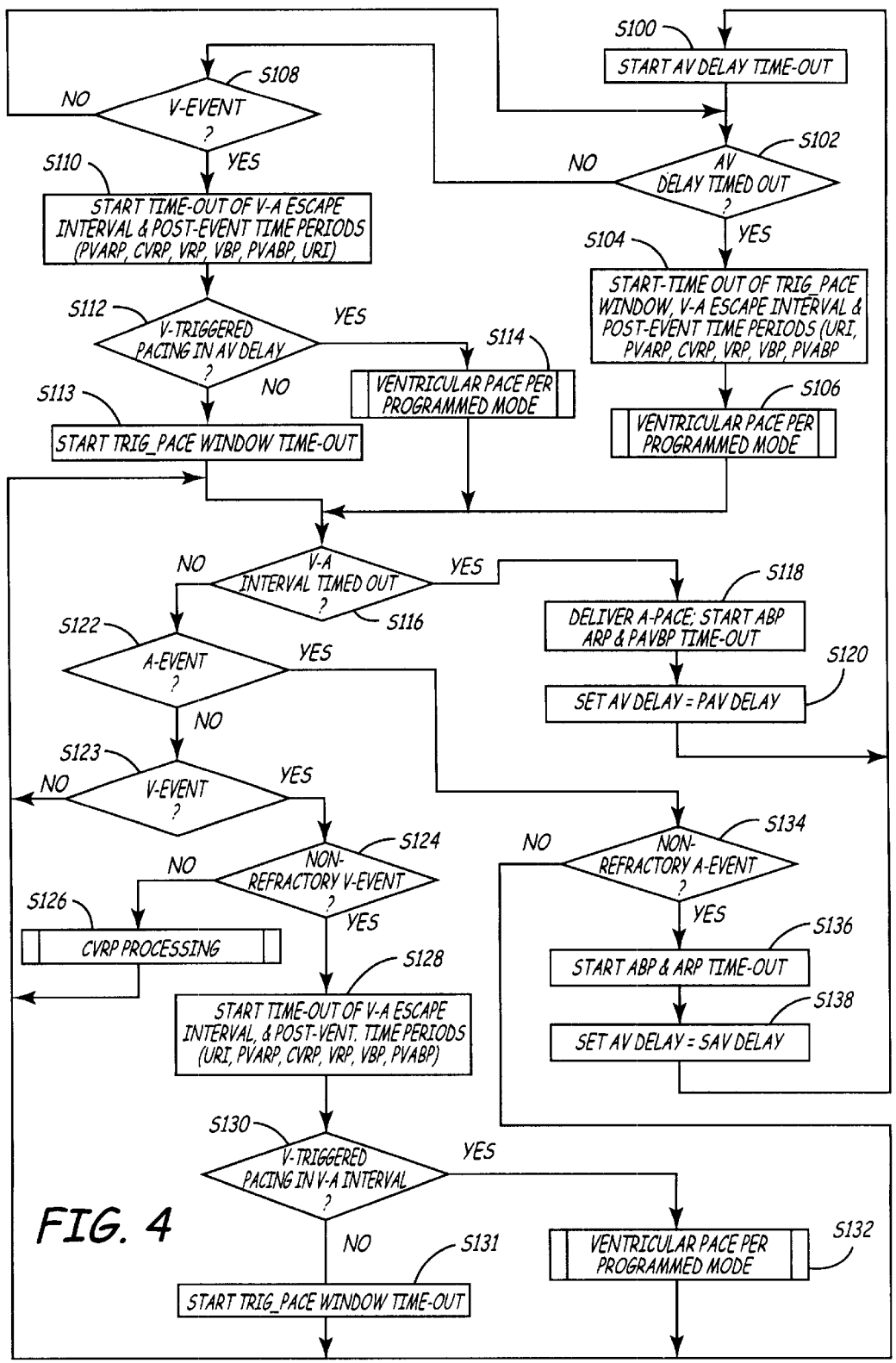
FIG. 4 is a comprehensive flow-chart illustrating the operating modes of the IPG circuitry of FIG. 3 in a variety of AV synchronous, bi-ventricular pacing modes in accordance with one embodiment of the invention.

FIG. 6A–6B is a flow chart illustrating the steps S112 and S132 (when provided or programmed on) of FIG. 4 for delivering ventricular pace pulses triggered by a ventricular sense event in step S108 during the time-out of an AV delay or in step S124 during time-out of the V-A escape interval. As noted above, the sensing of R-waves in the RV and LV can be accomplished employing several RV-SENSE and LV-SENSE sensing axes or vectors and the trans-ventricular sensing vector. A bipolar RV-SENSE vector (RV sense electrodes 38 and 40), a unipolar RV-SENSE vector (RV tip sense electrode 40 and IND_CAN electrode 20), and a unipolar LV-SENSE vector (LV sense electrode 50 and IND_CAN electrode 20), and a trans-ventricular, combined RV-SENSE and LV-SENSE vector (RV tip sense electrode 40 and LV sense electrode 50) can be programmed.

The IPG circuit 300 can be separately programmed in one of three triggered pacing modes designated VS/VP, VS/VP-VP or VS-VP triggered modes for step S114. In the VS/VP triggered pacing mode, a V-PACE1 is delivered without delay upon a RV-EVENT or LV-EVENT to the RV or LV pacing pathway, respectively. In the VS/VP-VP triggered pacing mode, the V-PACE1 is delivered without delay upon a RV-EVENT or LV-EVENT to the selected RV or LV pacing electrode pair, respectively, and a V-PACE2 is delivered to the other of the selected LV or RV pacing electrode pair after the VS/VP-VP delay times out. In the VS-VP pacing mode, a RV-EVENT or the LV-EVENT starts time-out of a VS-VP delay, and a single pace pulse (designated V-PACE2) is delivered to the selected LV or the RV pace electrode pair, respectively, when the VS-VP delay times out.

The TRIG_PACE time window started by a prior V-EVENT or V-PACE must have timed out in step S300 prior to delivery of any triggered ventricular pace pulses. If it has not timed out, then triggered pacing cannot be delivered in response to a sensed V-EVENT. If the TRIG_PACE window has timed out, it is then restarted in step S302, and the programmed triggered pacing modes are checked in steps S304 and S316.

When IPG circuit 300 is programmed in the VS/VP-VP triggered mode as determined in step S304, the non-refractory RV-EVENT or LV-EVENT or collective V-EVENT of indeterminable origin is treated as a single V-EVENT. If the TRIG_PACE window has timed out as determined in step S300, then the single V-EVENT triggers the immediate delivery of a programmed one of the RV-PACE or a LV-PACE as V-PACE1 across the programmed bipolar or unipolar RV and LV pace electrode pair, respectively, in step S306. Thus, V-PACE1 is delivered to a predetermined RV or LV pace electrode pair, regardless of whether a RV-EVENT and LV-EVENT is sensed.

Then, a VS/VP-VP delay is started in step S308 and timed out in step S310. The VS/VP-VP delay is specified as a VP-VP delay when the RV-PACE is V-PACE1 and the LV-PACE is V-PACE2. The VS/VP-VP delay is specified as a VP-VP delay when the LV-PACE is V-PACE1 and the RV-PACE is V-PACE2. The LV-PACE or RV-PACE pulse is delivered at the programmed amplitude and pulse width across the programmed LV or RV pace electrode pair in step S210.

In the simplest embodiment of the present invention, the VS/VP-VP mode would be the only triggered ventricular pacing mode provided. The remaining steps of FIGS. 6A and 6B are described in the event that the VS/VP and/or the VS-VP triggered ventricular pacing mode is included in the pacing system.

In step S314, it is determined whether the VS-VP triggered pacing mode or the VS/VP triggered pacing mode is programmed. When the IPG circuit 300 is programmed to a single heart chamber VS/VP triggered pacing mode, the RV-EVENT or LV-EVENT triggers the immediate delivery of an RV-PACE or an LV-PACE across a programmed bipolar or unipolar RV or LV pace electrode pair, respectively, in step S316, regardless of whether an RV-EVENT or LV-EVENT was sensed.

When the IPG circuit 300 is programmed to the VS-VP triggered pacing mode, an LV-EVENT as determined in step S318 loads the appropriate VS-VP delay in V-V delay timer 366 in step S320 and starts the VS-VP delay time-out in step S322. The RV-PACE is delivered at its time-out in step S322 (also designated V-PACE2). If an RV-EVENT is determined in step S318, then the appropriate VS-VP delay in V-V delay timer 366 in step S326 and the VS-VP delay is timed out in step S328. The LV-PACE (also designated V-PACE2) is delivered at time-out of the VS-VP delay in step S330.

Returning to FIG. 4, the V-A escape interval is timed out in step S116 following the completion of the ventricular pacing mode of FIGS. 6A–6B. If the V-A escape interval times out, then an RA pace pulse is typically first delivered across the RA pace electrodes 17 and 19 in step S118, and the AV delay timer is restarted in step S100.

The preceding specific embodiments are illustrative of the practice of the invention. It is to be understood, therefore, that other expedients known to those of skill in the art or disclosed herein may be employed.

The preceding specific embodiments are directed to RV and LV pacing in the predetermined sequence upon a sense event sensed in either or across the RV and LV. However, it will be understood that the present invention also embraces locating first and second ventricular pace/sense electrodes in either the RV or LV separated apart from one another. In this case, the V-PACE1 and/or V-PACE2 are delivered in one of the VS/VP. VS/VP-VP or VS-VP triggered pacing modes to the first and/or second ventricular pace/sense electrodes to provide for triggered pacing on a V-EVENT detected during the AV delay only.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of an AV synchronous pacemaker that are not disclosed and are not necessary to the practice of the present invention. In addition, it will be understood that specifically described structures, functions and operations set forth in the above-listed, commonly assigned and co-pending patent applications can be practiced in conjunction with the present invention, but they are not essential to its practice.

In the following claims, means-plus-function clauses are intended to cover the structures described herein as performing the recited function and not only structural equivalents but also equivalent structures.

It is therefore to be understood, that within the scope of the appended claims, the invention may be practiced otherwise than as specifically described without actually departing from the spirit and scope of the present invention.

What is claimed is:

1. In a multi-site, AV sequential, cardiac pacemaker, a method of selectively sensing spontaneous ventricular cardiac depolarizations at spaced apart ventricular sites and delivering pace pulses to the spaced apart ventricular sites for improving the hemodynamic efficiency of a sick heart suffering from conduction delays in conducting spontaneous or evoked depolarizations through the ventricles that compromise cardiac output, wherein said method comprises the steps of:

sensing spontaneous atrial depolarizations and providing atrial sense event signals;

timing out an AV delay from the atrial sense event signals;

sensing spontaneous cardiac depolarizations at a first ventricular site and providing first ventricular sense event signals;

sensing spontaneous cardiac depolarizations at a second ventricular site and providing second ventricular sense event signals;

upon provision of a first or second ventricular sense event signal during the timing out of the AV delay, delivering a ventricular pace pulse to a predetermined one of the first and second ventricular sites without delay;

upon time-out of the AV delay, delivering a ventricular pace pulse to a predetermined one of the first and second ventricular sites; and timing out a V-A escape interval establishing a pacing rate from a selected one of the first and second ventricular sense event signals provided during the AV delay and during the time-out of the V-A escape interval, whereby triggered ventricular pacing is only provided to at least one of the first and second ventricular sites only when a first or second ventricular sense event signal is provided during time-out of the AV delay.

2. The method of claim 1, wherein said first ventricular site is a right ventricular site in or adjacent to the right ventricle and said second ventricular site is a left ventricular site in or adjacent to the left ventricle; and the first ventricular sense event signals are right ventricular sense event signals, and the second ventricular sense event signals are left ventricular sense event signals, whereby spontaneous cardiac depolarizations of the right and left ventricles are sensed and pace pulses are delivered to the right and left heart ventricles for improving the hemodynamic efficiency of a sick heart suffering from conduction delays in conducting spontaneous or evoked depolarizations through the right and left ventricles that compromise cardiac output.

3. The method of claim 2, wherein the step of delivering a ventricular pace pulse to a predetermined one of the first and second ventricular sites upon provision of a first or second ventricular sense event signal during the timing out of the AV delay further comprises:

delivering a first pace pulse either as a right ventricular pace pulse to the right ventricular site to evoke a right ventricular depolarization or as a left ventricular pace pulse to the left ventricular site to evoke a left ventricular depolarization.

4. The method of claim 2, wherein the step of delivering a ventricular pace pulse to a predetermined one of the first and second ventricular sites upon provision of a first or second ventricular sense event signal during the timing out of the AV delay further comprises:

delivering a first ventricular pace pulse to a predetermined one of the right and left ventricular sites upon provision of a right or left ventricular sense event signal;

commencing and timing out a triggered pacing delay upon provision of a right or left ventricular sense event signal during the timing out of the AV delay; and at the time-out of the triggered pacing delay, delivering a pace pulse to the other of the right and left ventricular sites to evoke a synchronized depolarization of the right and left ventricles.

5. The method of claim 1, wherein the step of delivering a ventricular pace pulse to a predetermined one of the first and second ventricular sites upon provision of a first or second ventricular sense event signal during the timing out of the AV delay further comprises:

delivering a first ventricular pace pulse to a predetermined one of the first and second ventricular sites upon provision of a first or second ventricular sense event signal;

commencing and timing out a triggered pacing delay upon provision of a right or left ventricular sense event signal during the timing out of the AV delay; and at the time-out of the triggered pacing delay, delivering a pace pulse to the other of the first and second ventricular sites.

6. In a multi-site cardiac pacemaker, a pacing system for selectively sensing spontaneous ventricular cardiac depolarizations at spaced apart ventricular sites and delivering pace pulses to the spaced apart ventricular sites for improving the hemodynamic efficiency of a sick heart suffering from conduction delays in conducting spontaneous or evoked depolarizations through the ventricles that compromise cardiac output, wherein said pacemaker further comprises:

an atrial pace/sense lead adapted to be advanced into relation with an atrial chamber to situate an atrial pace/sense electrode in or adjacent to the atrial chamber;

ventricular pace/sense lead means for situating a first ventricular pace/sense electrode at a first ventricular site and a second ventricular pace/sense electrode at a second ventricular site spaced from said first ventricular site; and a pace pulse generator coupled to said atrial pace/sense lead and said ventricular pace/sense lead means comprising:

an atrial sense amplifier coupled to said atrial pace/sense electrode for sensing spontaneous atrial depolarizations and providing atrial sense event signals;

an AV delay timer for timing out an AV delay from the atrial sense event signals;

a first ventricular sense amplifier coupled to said first ventricular pace/sense electrode for sensing spontaneous cardiac depolarizations at the first ventricular site and providing first ventricular sense event signals;

a second ventricular sense amplifier coupled to said second ventricular electrode for sensing spontaneous cardiac depolarizations at the second ventricular site and providing second ventricular sense event signals;

an escape interval timer for timing out a V-A escape interval establishing a pacing rate from one of the first and second ventricular sense event signals occurring during the time-out of the AV delay or the V-A escape interval;

ventricular trigger pacing means coupled to said ventricular pace/sense lead means and operable in response to provision of a first or second ventricular sense event signal during the time-out of the AV delay for delivering a ventricular pace pulse to a predetermined one of said first and second pace/sense electrodes at said first and second ventricular sites without delay; and V-A escape interval restarting means operable in response to provision of a first or second ventricular sense event signal during the time-out of the V-A escape interval for terminating and restarting the V-A escape interval, whereby triggered ventricular pacing is provided to at least one of the first and second ventricular sites only when a first or second ventricular sense event signal is provided during time-out of the AV delay.

7. The pacing system of claim 6, wherein said ventricular trigger pacing means further comprises:

means for delivering a first ventricular pace pulse to a predetermined one of the first and second ventricular sites upon provision of a first or second ventricular sense event signal;

a trigger delay timer for commencing and timing out a triggered pacing delay upon provision of a right or left ventricular sense event signal during the timing out of the AV delay; and means operable upon time-out of the triggered pacing delay for delivering a pace pulse to the other of the first and second ventricular sites.

8. The pacing system of claim 6, wherein said first ventricular site is a right ventricular site in or adjacent to the right ventricle and said second ventricular site is a left ventricular site in or adjacent to the left ventricle; and the first ventricular sense event signals are right ventricular sense event signals, and the second ventricular sense event signals are left ventricular sense event signals, whereby spontaneous cardiac depolarizations of the right and left ventricles are sensed and pace pulses are delivered to the right and left heart ventricles for improving the hemodynamic efficiency of a sick heart suffering from conduction delays in conducting spontaneous or evoked depolarizations through the right and left ventricles that compromise cardiac output.

9. The pacing system of claim 8, wherein said ventricular trigger pacing means further comprises:

means for delivering a first pace pulse either as a right ventricular pace pulse to the right ventricular site to evoke a right ventricular depolarization or as a left ventricular pace pulse to the left ventricular site to evoke a left ventricular depolarization.

10. The pacing system of claim 8, wherein said ventricular trigger pacing means further comprises:

means for delivering a first ventricular pace pulse to a predetermined one of the right and left ventricular sites upon provision of a right or left ventricular sense event signal;

a trigger delay timer for commencing and timing out a triggered pacing delay upon provision of a right or left ventricular sense event signal during the timing out of the AV delay; and means operable upon time-out of the triggered pacing delay for delivering a pace pulse to the other of the right and left ventricular sites to evoke a synchronized depolarization of the right and left ventricles.

\* \* \* \* \*